United States Patent [19]
Apfel

[11] Patent Number: 5,004,538
[45] Date of Patent: Apr. 2, 1991

[54] CONTROL ARRANGEMENT FOR THE CHROMATOGRAPHY OF LIQUID

[76] Inventor: Helmut Apfel, Loheweg 5, 8039 Puchheim, Fed. Rep. of Germany

[21] Appl. No.: 492,319

[22] Filed: Mar. 2, 1990

Related U.S. Application Data

[63] Continuation of Ser. No. 245,300, Sep. 16, 1988, abandoned.

[30] Foreign Application Priority Data

Mar. 12, 1986 [DE] Fed. Rep. of Germany ........ 3608227

[51] Int. Cl.$^5$ ............................................. B01D 15/08
[52] U.S. Cl. ................................ 210/198.2; 210/101; 210/656; 73/861.05
[58] Field of Search .................... 73/861.05; 210/656, 210/659, 198.2, 101

[56] References Cited

U.S. PATENT DOCUMENTS

| | | | |
|---|---|---|---|
| 3,403,555 | 10/1968 | Versaci | 73/861.05 |
| 3,621,715 | 11/1971 | Soderkvist | 73/861.05 |
| 3,688,574 | 9/1972 | Arutunian | 73/861.05 |
| 3,739,636 | 6/1973 | Versaci | 73/861.05 |
| 3,815,414 | 6/1974 | Hellstrom | 73/861.05 |
| 3,917,351 | 11/1975 | Magnussen | 210/198.2 |
| 4,104,914 | 8/1978 | McClure | 73/861.05 |
| 4,145,923 | 3/1979 | McClure | 73/861.05 |
| 4,357,668 | 11/1982 | Schwartz | 210/198.2 |
| 4,487,075 | 12/1984 | Karidis | 73/861.05 |
| 4,559,831 | 12/1985 | Prestele | 73/861.05 |
| 4,699,768 | 10/1987 | Weiss | 210/198.2 |
| 4,733,152 | 3/1988 | Allington | 210/198.2 |
| 4,762,617 | 8/1988 | Allington | 210/198.2 |
| 4,767,279 | 8/1988 | Dourdeville | 210/198.2 |
| 4,772,388 | 9/1988 | Allington | 210/198.2 |
| 4,775,481 | 10/1988 | Allington | 210/198.2 |
| 4,781,824 | 11/1988 | Allington | 210/198.2 |

FOREIGN PATENT DOCUMENTS

| | | | |
|---|---|---|---|
| 3226398 | 6/1985 | Fed. Rep. of Germany | 210/198.2 |
| 3346198 | 7/1985 | Fed. Rep. of Germany | 210/198.2 |
| 3608227 | 9/1987 | Fed. Rep. of Germany | 210/198.2 |

OTHER PUBLICATIONS

Snyder, Introduction to Modern Liquid Chromatography, John Wiley & Sons, Inc., New York, 1979, pp. 542-560.
Perry's Chemical Engineer's Handbook, Fourth Edition, McGraw Hill, New York, 1969, pp. 2-7.

*Primary Examiner*—Ernest G. Therkorn
*Attorney, Agent, or Firm*—Evenson, Wands, Edwards, Lenahan & McKeown

[57] ABSTRACT

A control arrangement for a liquid chromatograph is disclosed which generates a correction factor to compensate for non-uniform passage of eluate past the detector of the chromatograph. A flow meter measures the actual flow of eluate from the detector and generates a representative signal which is compared with a standard signal representative of the desired flow rate to generate the correction signal.

5 Claims, 1 Drawing Sheet

CONTROL ARRANGEMENT FOR THE CHROMATOGRAPHY OF LIQUID

This is a continuation of application Ser. No. 245,300, filed, Sept. 16, 1988, now abandoned.

BACKGROUND AND SUMMARY OF THE INVENTION

The invention generally relates to a control arrangement for the chromatography of liquids which compensates for the non-uniform passage of a specimen past the detector of a liquid chromatograph and, more particularly to a flow meter control arrangement capable of measuring very small flow rates to determine a valid correction factor.

Chromatographs for liquids are known, such as disclosed in German Patent (DE-PS) 32 26 398, wherein a specimen of closely related compounds is separated into its individual fractions by charging a separation column with the specimen and introducing a solvent into the separator column so that the resulting eluate, i.e., specimen and solvent, can be analyzed by successively passing each fraction of the specimen past a detector. In the case of known liquid chromatographs, to assure accurate analysis of the specimen, it is important that the individual fractions of the specimen measured by the chromatograph are each moved past the detector along at a uniform speed. Otherwise the analysis, which takes place by integrating the so-called peak areas of the signals generated by the detector, is falsified and the peak bases for each individual fraction become either too narrow or too wide. In the case of known liquid chromatographs, uniform passage of the fractions of the specimen past the detector has been accomplished by use of a removal device provided on the side of the detector that is connected to the outlet duct. This removal device ensures a discharge volume that is in each case constant for each time unit. While the above-noted known liquid chromatograph works very accurately, one particular drawback of this arrangement is that relatively high expenditures and complexity of equipment are required in order to ensure a constant flow rate.

Therefore, one object of the present invention is to provide an arrangement which compensates for the non-uniform passage of a specimen past the detector of a liquid chromatograph that is simple and eliminates the need for an expensive and complex removal control device connected to the outlet or exhaust line of the chromatograph.

In order to achieve this object, the present invention utilizes a unique approach for measuring the actual rate of flow of the eluate past the detector of the chromatograph. By means of this development, the respective deviation of the actual flow rate and of the desired flow rate can be determined and represented as a correction factor to provide an arrangement which compensates for non-uniform flow and is technically easier to implement than the previously known removal control device. When the actual flow rate and the desired flow rate correspond to one another, the correction factor is $f=1$. As used hereinafter, this correction factor f is defined as:

$$f = \frac{FRi}{FRs}$$

wherein FRi is the actual flow rate and FRs is the desired flow rate. The determination of the correction factor f is accomplished by a special flow meter which is capable of exactly determining small flow values. This flow meter can be used for determining the flow in devices other than liquid chromatographs; however, it is particularly advantageous for use in the chromatography of liquids.

One particular advantage of the present invention is that the flow meter, at any given moment during the analysis of a specimen, is capable of providing a computer or data station with the current or present valid correction factor f for processing the measured values generated from the detector. This arrangement permits the integrator of the analyzing device to operate correctly in real-time even if the actual flow rate deviates considerably from the desired flow rate. During normal use, if the work takes place in the normal manner and at a constant pressure upstream of the separation column, the deviations from the desired flow rate are not extreme. However, the individual retention times of each individual fraction of the specimen, which are used for peak identification, cannot remain uncorrected in order to assure accurate analysis of the specimen. Therefore, during the correction, the respective deviations from the desired flow rate are entered into the computation of the relative retention times and further, this process can also be fully automated by means of the appropriate hardware or software.

Another advantage of preferred embodiments of the present invention consists of using the value of the retention volume instead of the value of the retention time for peak identification. It was found that under defined conditions (column, temperature, elutriating agent, admission pressure), and also when the flow rates are fluctuating, the elutriating agent volume, which is required for moving a certain fraction through the column, fluctuates only very little. With this aforementioned approach, the flow rate can be changed without any damaging effect during an analysis, and in many cases, results in an important improvement with respect to the separation quality and the analysis time. Often, late-elutriating fractions, which require a relatively long waiting period are of special interest. By the intentional increase of the flow rate during the run, the late fractions can be elutriated off much faster. The gradients for the elutriating agent mixture and for the column temperature, which are used in methods of the conventional chromatography of liquids, are therefore joined by the flow rate gradient as a third gradient. This additional degree of freedom in the shaping of the analysis parameters opens up new possibilities for the optimizing of the chromatography of liquids.

Other objects, advantages and novel features of the present invention will become apParent from the following detailed description of the invention when considered in conjunction with the accompanying drawings.

DETAILED DESCRIPTION OF THE DRAWINGS

Figure 1:
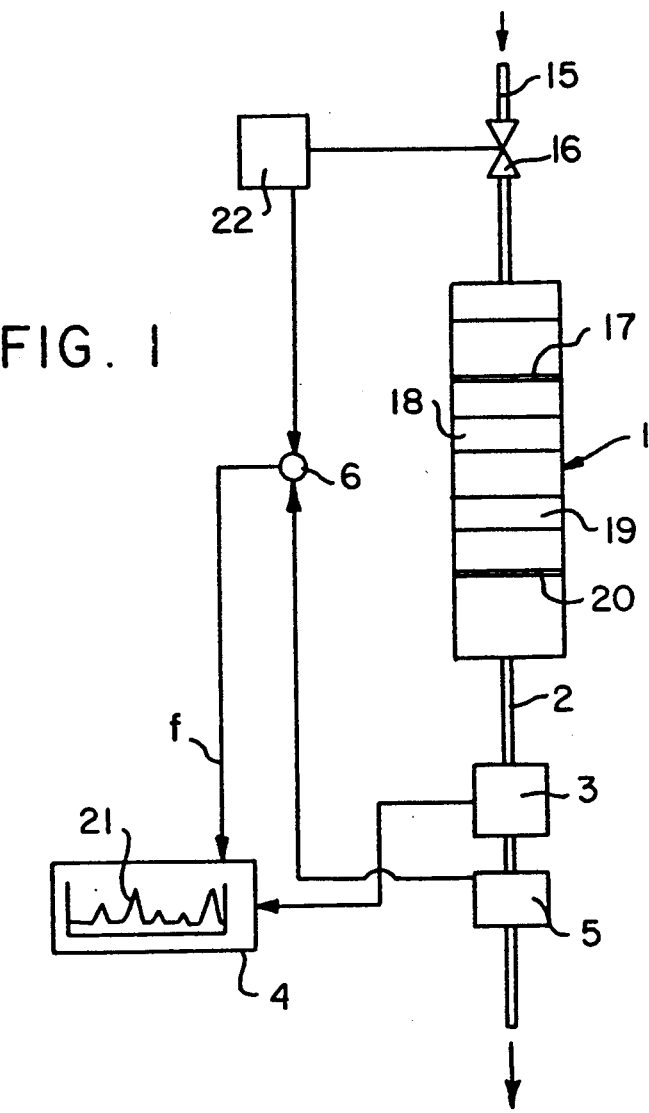
FIG. 1 is a schematic representation of the present invention utilizing a block diagram to illustrate a new arrangement for the chromatography of liquids.

In the basic diagram of FIG. 1, a separation column, generally indicated by reference numeral 1, is shown to which, in a known manner, an elutriating agent from a high-pressure tank is admitted via feed or inlet line 15. In the separation column 1, a specimen is located, the separated, individual fractions of the specimen, as designated by reference numerals 17, 18, 19, 20, respectively, move through the separation column, emerging from the separation column 1, together with the eluate. The fractions 17, 18, 19, 20 of the specimen and the elutriating agent, arrive in outlet duct 2 on the low-pressure side of the separation column 1 and then successively move past detector 3. In an analysis device 4 of the detector 3, the substance concentrations of the fractions are recorded in the direction of the ordinate, and the volume of the fractions is recorded in the direction of the abscissa of a diagram. The areas of resulting peaks 21 are integrated and result in the amounts of substance to be determined which were contained in the specimen.

Downstream from detector 3, in accordance with the present invention, a flow meter 5 is inserted in the outlet duct 2 downstream of separation column 1. This flow meter 5 measures the flow rate occurring at the outlet of the detector 3 and provides the measured value to a comparison device 6 such as, for example, a differential amplifier or comparator, to which the value of a desired flow rate is provided as the comparative value. The value of the desired flow rate, for example, is stored in a memory device 22 in which a given value is inputted. This static or calculated desired flow rate value may be generated from known parameters for a given chromatographic device or method.

Alternatively, a dynamic or actual desired flow rate value can be provided to memory device 22 as explained below. The user starts his analysis with (arbitrarily preselectable) parameters for the pressure, to which he subjects the elutriant entering into the column, or for the volumetric displacement which he assigns to the chromatography high-pressure pump which is arranged upstream of the column 1 but is not shown.

An actual flow rate value is obtained at the start of the analysis which is measured by means of the flow meter 5. This initial flow rate value is then used as the desired flow rate value and is stored in the memory device 22.

The comparison device 6 generates a signal indicative of a correction factor f $$f = \frac{FRi}{FRs}$$

from the actual flow rate FRi generated by the flow meter 5, and from the desired flow rate FRs coming from the device 22, and transmits the correction factor f signal to the analysis device 4 having an integrator, which is capable, by means of this correction factor, of ensuring that deviations of the actual flow rate at the detector 3 from the desired flow rate do not lead to a falsification of the analysis result by altering the time interval of integrator to correspond to the actual flow rate of eluate past detector 3.

Typically, the flow rates occurring in the duct 2 during the chromatography of liquids are very low. They may fall to 0.1 microliters per second. The flow meter 5 must be able to measure these low microquantities. For this purpose the new flow meter for microquantities is used which is shown in diagram form in FIG. 2.

Figure 2:
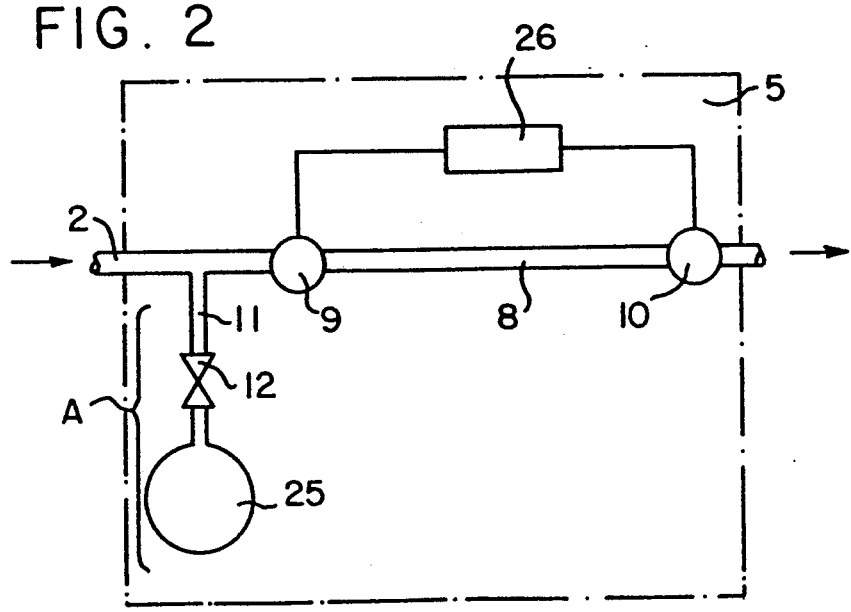
FIG. 2 is a schematic representation of the flow meter used in the present invention.

Referring to FIG. 2, in the case of flow meter 5, the liquid to be measured flows through a duct which, for example, adjoins the duct 2 of FIG. 1 directly downstream from the detector 3. As best seen in FIG. 2, the duct forms a measuring section 8 which may consist, for example, of a teflon hose having an inside width of approximately 0.3 mm. However, the use of a capillary glass tube or the like is also possible, providing the tube has the transparency required for the optical sensors. This measuring section 8 is bordered by sensors 9 and 10, respectively, such as disclosed, for example, by DE-OS 33 46 198. Upstream of the sensor 9 is a bubble generator, generally at A, having a duct 11 leading into the outlet duct 2; duct 11 conducting a gaseous medium, such as air or helium into outlet duct 2 to form uniform gas bubbles. This gaseous medium is located in a schematically represented tank 25 having a given, but low positive pressure and, via a valve 12, such as a solenoid valve, can be fed, for a short time and in the form of short gas bubbles, into the flow duct 2. These gas bubbles will then move past the sensor 9 and the measuring section 8 before they flow past the sensor 10.

The two sensors 9 and 10 are designed such that they recognize the leading edge or front of the gas bubble. Both sensors, when detecting a certain point of the gas bubble, which is the same for both sensors, each forward a signal to data station or computer 26, in which the time needed for a gas bubble to pass through the measuring section 8 is recorded. Since the dimensions of the measuring section 8 are fixed, the computer 26 can calculate the amount of liquid which has passed through the flow meter 5 in the measured time. This value, the so-called actual flow rate, is then fed to the comparison device 6.

Since, in flow meter 5, time is measured instead of actual fluid flow, this time signal is directly proportional to the actual flow rate and, may be fed directly to the comparison device 6 instead of the calculated flow rate. In this embodiment, the value stored in the memory device 22, will be a time signal which is arbitrarily preselectable and derived from the desired flow rate which is preferably constant during analysis. Thus, the signal generated by the memory device 22 remains constant. The comparison device 6 may, for example, be constructed as an electronic comparator which compares the desired time ts for the passage of the air bubbles through the measuring section stored in the memory device 22 with the actual passage times ti furnished by the flow meter 5.

The deviation of the actual flow from the desired flow rate in percent is obtained by means of the following formula:

$$\frac{(ts - ti) \times 100}{ti} = \text{deviation in percent of desired value.}$$

In this embodiment of the present invention, the value $$\frac{ts}{ti}$$

is used as the correction value with which individual integration values are multiplied by the analysis device 4, in order to provide real-time correction of any measuring errors caused by flow rate fluctuations. The flow meter of FIG. 2 is not limited for use in the chromatography of liquids; however, it is particularly advantageous in this case.

The data station or computer 26 furnishes a correction factor T control signal representative of the deviation of the actual passage time ti and the desired passage time ts, which has a duration and sign value proportional to the deviation. This correction factor T control signal may be used as a feed-back control signal to set the actual flow rate equal to the desired flow rate, whereby the flow meter becomes a flow governor. For this purpose, the control signal is inputted to the drive of a suitable control element (such as a needle valve) in the control circuit, for example, on the valve 16. This control circuit must be damped in order to exclude an overshot. In such an arrangement, which controls the flow, the correction factor f, in addition, may also be determined, as explained above and used to control the flow. However, the then existing deviations between the actual flow rate and the desired flow rate may be kept at zero.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A control arrangement for a liquid chromatograph to compensate for non-uniform flow rates past a chromatograph detector, said arrangement comprising:
   (a) a separation column having an inlet for receiving a solvent and an outlet for discharging an eluate, said separation column being adapted to be charged with a specimen to be separated into its individual fractions;
   (b) a detector for detecting each fraction of the specimen in the eluate and for generating a detector signal proportional to the substance concentrations of the fractions as well as the volume of each fraction;
   (c) an analyzing device having an integrator for integrating said detector signal over a given time interval to provide an integrator output value indicative of the quantity of substance to be determined contained in the specimen;
   (d) a flow meter for determining the actual flow rate of eluate past said detector for a given time period and for generating a signal representative of a desired flow rate;
   (e) a standard flow rate signal generator for providing a standard signal representative of a desired flow rate;
   (f) a comparator for generating a correction factor signal equal to the ratio of said actual flow rate signal to said standard signal for a given time interval; and
   (g) compensating means for compensating for variations in the actual flow rate from the standard flow rate by directly correcting the integrator output value as a function of the correction factor to alter the time interval of the integrator to correspond to the actual flow rate of eluate past the detector to permit the integrator of the analyzing device to operate correctly in real time even when the actual flow rate deviates from the desired flow rate.

2. A control arrangement according to claim 1, wherein said flow meter comprises:
   (a) a duct having a given inside diameter for receiving eluate from said detector;
   (b) a measuring section formed from a given length of said duct and bordered by sensors adapted to detect air bubbles in said duct;
   (c) a bubble generator for forming bubbles in said duct, said bubble generator having a gas supply under pressure connected to said duct by a valve adapted to pass gas into said duct for constant time intervals to form a series of bubbles; and
   (d) means for measuring the time interval it takes a bubble to pass by a given point of each sensor bordering said measuring section, and for generating a signal representation of said measured time interval.

3. A control arrangement according to claim 2, wherein said flow meter further comprises means for calculating and generating a signal representative of the actual flow rate of the eluate through said duct by multiplying the given diameter of said duct with the length of said measuring section divided by said measured time interval.

4. A control arrangement according to claim 2, wherein said measuring section is formed from a tube capable of transmitting light through the tube wall.

5. A control arrangement according to claim 1, wherein said compensating means further comprise a solvent control arrangement for controlling the flow rate of solvent to said inlet of said separator column to provide uniform flow of eluate past said detector.

* * * * *